(12) United States Patent
Ebrahimi et al.

(10) Patent No.: US 10,869,679 B2
(45) Date of Patent: Dec. 22, 2020

(54) POSITIONING AND ALIGNMENT INSTRUMENT FOR INTRODUCING SURGICAL DEVICES INTO BONE

(71) Applicant: SUNNYBROOK RESEARCH INSTITUTE, Toronto (CA)

(72) Inventors: Hamid Ebrahimi, Toronto (CA); Cari Marisa Whyne, Toronto (CA); Albert J. M. Yee, Toronto (CA)

(73) Assignee: SUNNYBROOK RESEARCH INSTITUTE, Toronto (CA)

( * ) Notice: Subject to any disclaimer, the term of this patent is extended or adjusted under 35 U.S.C. 154(b) by 32 days.

(21) Appl. No.: 16/077,470

(22) PCT Filed: Feb. 17, 2017

(86) PCT No.: PCT/CA2017/050216
§ 371 (c)(1),
(2) Date: Aug. 11, 2018

(87) PCT Pub. No.: WO2017/139901
PCT Pub. Date: Aug. 24, 2017

(65) Prior Publication Data
US 2019/0069911 A1    Mar. 7, 2019

Related U.S. Application Data

(60) Provisional application No. 62/297,571, filed on Feb. 19, 2016.

(51) Int. Cl.
*A61B 17/17* (2006.01)
*A61B 17/92* (2006.01)

(52) U.S. Cl.
CPC ...... *A61B 17/1717* (2013.01); *A61B 17/1703* (2013.01); *A61B 17/1725* (2013.01);
(Continued)

(58) Field of Classification Search
CPC . A61B 17/17; A61B 17/1703; A61B 17/1717; A61B 17/1725; A61B 17/1728;
(Continued)

(56) References Cited

U.S. PATENT DOCUMENTS 4,383,527 A     5/1983  Asnis et al.
4,865,025 A *   9/1989  Buzzi ................ A61B 17/1703
                                            606/96

(Continued)

FOREIGN PATENT DOCUMENTS

CN    104983459 A   10/2015
EP      2742877 A1   6/2014
(Continued)

OTHER PUBLICATIONS

Ebrahimi et al., Int. J. Comput. Assist. Radiol. Surg., "Surgical process analysis identifies lack of connectivity between sequential fluoroscopic 2D alignment as a critical impediment in femoral intramedullary nailing", Feb. 2016; 11(2):297-305.
(Continued)

*Primary Examiner* — Larry E Waggle, Jr.
(74) *Attorney, Agent, or Firm* — Hill & Schumacher

(57) ABSTRACT

A positioning and alignment instrument, and methods of use thereof, are provided for facilitating the alignment and insertion of a device, such as a guide wire, into bone. The instrument includes a handheld anchoring component and a rotatable guidance component. During use, the anchoring component is anchored into bone via anchoring protrusions, such that the position and orientation of the anchoring component is fixed relative to the bone. The guidance component, which is mechanically supported by the anchoring component, includes a device guide channel for receiving the device and guiding the device towards an insertion location adjacent to the distal end of the anchoring compo-
(Continued)

nent. The guidance component is rotatable relative to the anchoring component about a rotation axis that is located adjacent to the distal end of the anchoring component, such that the insertion location remains adjacent to the distal end of the anchoring component under rotation.

37 Claims, 17 Drawing Sheets

(52) U.S. Cl.
CPC ........ *A61B 17/1739* (2013.01); *A61B 17/921* (2013.01); *A61B 17/1728* (2013.01)

(58) Field of Classification Search
CPC ..... A61B 17/1739; A61B 17/72; A61B 17/92; A61B 17/921
See application file for complete search history.

(56) References Cited

U.S. PATENT DOCUMENTS

| | | | |
|---|---|---|---|
| 5,112,337 A | 5/1992 | Paulos et al. | |
| 5,152,766 A | 10/1992 | Kirkley | |
| 5,334,205 A * | 8/1994 | Cain | A61B 17/1739 606/86 R |
| 5,403,322 A | 4/1995 | Herzenberg et al. | |
| 5,613,971 A | 3/1997 | Lower et al. | |
| 5,643,273 A | 7/1997 | Clark | |
| 5,951,561 A | 9/1999 | Pepper et al. | |
| 6,342,057 B1 | 1/2002 | Brace et al. | |
| 6,740,120 B1 | 5/2004 | Grimes | |
| 7,575,578 B2 | 8/2009 | Wetzler et al. | |
| 7,981,114 B2 | 7/2011 | Zander | |
| 8,007,501 B2 | 8/2011 | Kaup et al. | |
| 8,273,091 B2 * | 9/2012 | Elghazaly | A61B 17/1725 606/96 |
| 8,308,732 B2 | 11/2012 | Millett | |
| 8,617,166 B2 | 12/2013 | Hanson et al. | |
| 8,771,283 B2 * | 7/2014 | Larsen | A61B 17/1725 606/96 |
| 8,821,504 B2 | 9/2014 | Sharkey et al. | |
| 8,864,768 B2 | 10/2014 | Hanson et al. | |
| 8,906,032 B2 | 12/2014 | Hanson et al. | |
| 8,986,316 B1 * | 3/2015 | Jordan | A61B 17/1714 606/96 |
| 9,241,744 B2 * | 1/2016 | Blake | A61B 17/7225 |
| 9,592,064 B2 * | 3/2017 | Biedermann | A61B 17/17 |
| 10,213,219 B2 * | 2/2019 | Garlock | A61B 17/88 |
| 2007/0270877 A1 | 11/2007 | Park | |
| 2009/0299416 A1 | 12/2009 | Hanni et al. | |
| 2011/0125160 A1 | 5/2011 | Bagga et al. | |
| 2012/0022543 A1 | 1/2012 | Porzel et al. | |
| 2014/0081281 A1 | 3/2014 | Felder | |

FOREIGN PATENT DOCUMENTS

| | | |
|---|---|---|
| EP | 2713908 B1 | 4/2015 |
| WO | 2013098853 A2 | 7/2013 |
| WO | 2015122807 A1 | 8/2015 |

OTHER PUBLICATIONS

International Search Report of the parent PCT application PCT/CA2017/050216, dated Jul. 17, 2017.

* cited by examiner

FIG. 3A
a
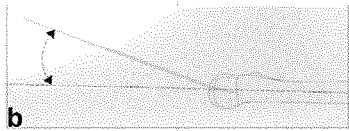
FIG. 3B
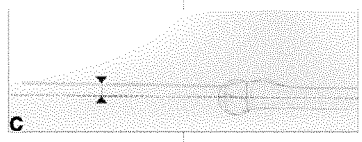
FIG. 3C
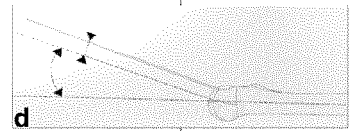
FIG. 3D
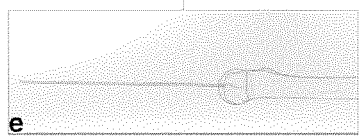
FIG. 3E

POSITIONING AND ALIGNMENT INSTRUMENT FOR INTRODUCING SURGICAL DEVICES INTO BONE

CROSS-REFERENCE TO RELATED APPLICATION

This application is a National Phase application claiming the benefit of the international PCT Patent Application No. PCT/CA2017/050216, filed on Feb. 17, 2017, in English, which claims priority to U.S. Provisional Application No. 62/297,571, titled "POSITIONING AND ALIGNMENT INSTRUMENT FOR INTRODUCING SURGICAL DEVICES INTO BONE" and filed on Feb. 19, 2016, the entire contents of which are incorporated herein by reference.

BACKGROUND

Intramedullary (IM) nailing is a minimally invasive surgical procedure typically performed under a general anesthetic and with fluoroscopic image guidance. The surgical phases associated with this type of surgery are well defined: patient preparation, access to the bone entry site, IM guide wire insertion (including fracture reduction for guide wire placement), IM nail placement, locking of the nail to control rotation and length, final clinical and radiographic assessment of fracture reduction/restoration of length/alignment/rotation, and surgical wound closure. Yet, despite widespread usage of IM nailing, significant surgical challenges may arise. Such challenges can significantly impede the surgical workflow, requiring additional operative time and radiation exposure to both patients and medical staff. Fracture reduction and proper localization for initial IM access are particularly challenging areas in the workflow pathway. Lengthy delays in the procedure and unacceptable fracture reduction or stabilization can also significantly endanger patient safety, particularly in those who may suffer from polytrauma and/or acute respiratory issues.

SUMMARY

A positioning and alignment instrument, and methods of use thereof, are provided for facilitating the alignment and insertion of a device, such as a guide wire, into bone. The instrument includes a handheld anchoring component and a rotatable guidance component. During use, the anchoring component is anchored into bone via anchoring protrusions, such that the position and orientation of the anchoring component is fixed relative to the bone. The guidance component, which is mechanically supported by the anchoring component, includes a device guide channel for receiving the device and guiding the device towards an insertion location adjacent to the distal end of the anchoring component. The guidance component is rotatable relative to the anchoring component about a rotation axis that is located adjacent to the distal end of the anchoring component, such that the insertion location remains adjacent to the distal end of the anchoring component under rotation.

Accordingly, in one aspect, there is provided a positioning and alignment instrument for guiding insertion of a device into bone, the positioning and alignment instrument comprising:

an anchoring component comprising a proximal portion and a distal portion, wherein said proximal portion comprises a handle, and wherein one or more anchoring protrusions extend from a distal end of said distal portion for anchoring said anchoring component into the bone, such that a position and an orientation of said anchoring component is fixed relative to the bone when said anchoring component is anchored to the bone; and a guidance component mechanically supported by said anchoring component, said guidance component comprising a device guide channel for receiving the device and guiding the device towards an insertion location adjacent to the distal end of said anchoring component;

wherein said guidance component is rotatable relative to said anchoring component about a rotation axis that is located adjacent to the distal end of said anchoring component, such that the insertion location remains adjacent to the distal end of said anchoring component under rotation of said guidance component.

In another aspect, there is provided a method of employing fluoroscopy to aligning a device during a medical procedure, the method comprising, after having employed fluoroscopy, in a first direction, to anchor the positioning and alignment instrument into bone:

obtaining fluoroscopy images of the positioning and alignment instrument in a perpendicular direction; and rotating the guidance component to a desired angle according to the fluoroscopy images; and thereby aligning the device guide channel for subsequent guidance and insertion of the device into the bone.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 3A-3E illustrate the steps and challenges in conventional Kirschner wire (K-wire) positioning and alignment. FIG. 3A shows an initial anterior-posterior (AP) image with a correct entry point location and orientation. Perpendicular lateral images through the sagittal plane show the following: FIG. 3B: correct location, incorrect orientation, requiring AP rotation; FIG. 3C: incorrect location, correct orientation, requiring AP translation; and FIG. 3D: incorrect location and orientation of the entry point, requiring AP rotation and translation to obtain correct lateral entry point location and orientation, shown in FIG. 3E.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Figure 1A:
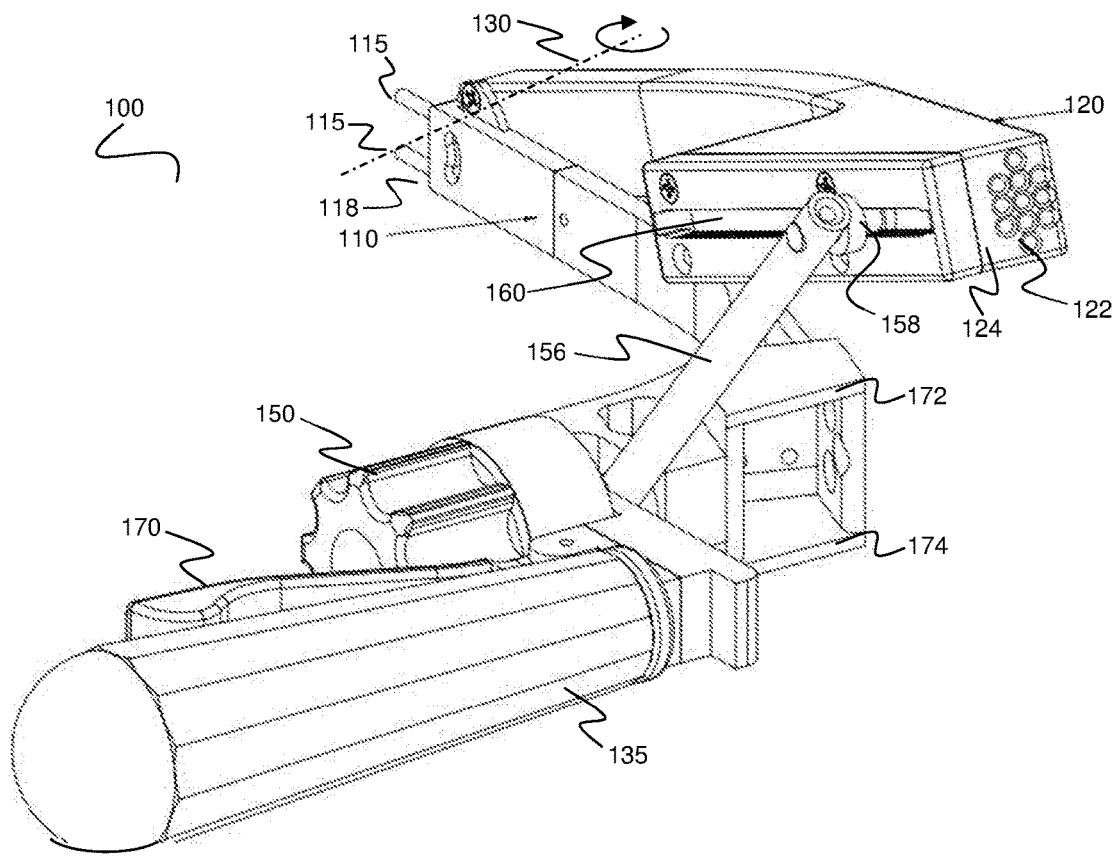
FIGS. 1A and 1B show views of an example positioning and alignment instrument.

Referring now to FIG. 1A, an example positioning and alignment instrument 100 is shown, where the instrument 100 is configured for facilitating the alignment and insertion of a device, such as a guide wire (not shown), into bone. The instrument 100 includes a handheld anchoring component 110 and a rotatable guidance component 120. During use, the anchoring component 110 is anchored into bone via anchoring protrusions 115, such that the position and orientation of the anchoring component 110 is fixed relative to the bone. The distal surface 118 of the anchoring component 110, from which the anchoring protrusions 115 extend, contacts the bone upon insertion of the anchoring component 110 into the bone, thereby establishing a reference location at the bone surface. In the example embodiment shown in FIGS. 1A and 1B, the distal end 118 of the anchoring component 110 has a rectangular cross-section.

Figure 1B:
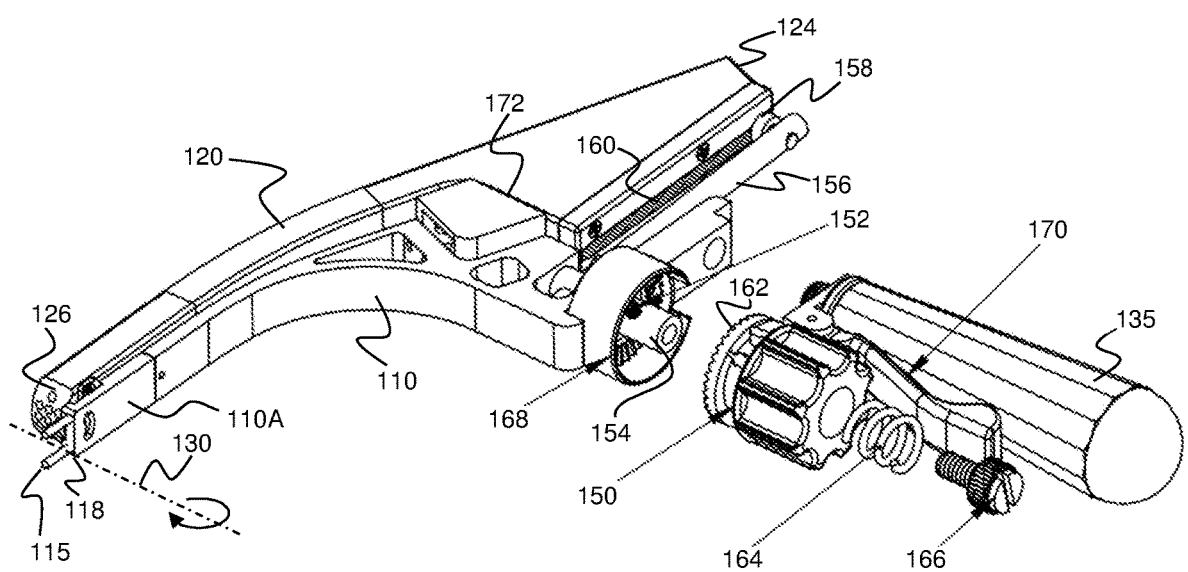

In the present example embodiment, the rotatable component 120 is a multi-cannulated arm that includes a plurality of device guide channels 122, where each device guide channel has a diameter suitable for receiving and guiding a device (e.g. a guide wire) as the device is advanced towards the bone. As shown in FIGS. 1A and 1B, each device guide channel 122 extends, through the rotatable guidance component 120, from a proximal end 124 to a distal end 126. As described in detail below, the optional inclusion of a plurality of device channel guides 122, arrayed in one or two dimensions, provides a surgeon with the ability to select a suitable device guide channel for device insertion in order to obtain a desired entry location relative to the anchoring location (the location in the bone that is adjacent to the distal end of the anchoring component 110). The diameters of the various device guide channels 122 may be identical or different, and may vary in terms of diameter, pattern and number.

For applications involving the use of fluoroscopy, such as those described below, at least a distal region of the rotatable guidance component 120 may be radiolucent, such that the device guide channels 122 and/or a device inserted within a given device guide channel 122 is observable. In such applications, it may be preferable for the distal ends of both the rotatable guidance component 120 and the anchoring component 110 to be radiolucent. For example, the distal region of the anchoring component 110 may include a radiolucent segment 110A. One of both of the rotatable guidance component 120 and the anchoring component 110 may include a radiopaque material in order to identify one or more features or locations of the positioning and alignment instrument.

The rotatable guidance component 120 is rotatable relative to the anchoring component 110, in order to vary the angular orientation of device channel guides 122 relative to the anchoring location, thereby enabling the selection of a suitable orientation for insertion (entry) of the device into the bone (e.g. a suitable angular orientation relative to the bone, or to internal anatomical features or structures, or to an internal medical device). As shown in FIGS. 1A and 1B, the rotatable guidance component 120 rotates about a rotation axis 130 that is located adjacent to the distal end 118 of the anchoring component 110. As used herein, the phrase "adjacent to the distal end 118 of the anchoring component" refers to a location that is at, or is proximal to, the distal end 118 of the anchoring component 110, such as within 5 mm, within 4 mm, within 3 mm, within 2 mm, or within 1 mm, of the distal end of the anchoring component. It will be understood that a suitable maximum offset of the rotation axis 130 relative to the distal end 118 of the anchoring component 110 may depend on clinical application. For example, in the case of the insertion of a guidewire (e.g. a Kirschner wire) during an intramedullary nailing procedure, a suitable maximum offset may be 10 mm.

By rotatably securing the rotatable guidance component 120 to the anchoring component 110 such that the rotation axis 130 lies adjacent to the distal end 118 of the anchoring component 110, the entry location of the device remains adjacent to the distal end of the anchoring component 110 over a wide range of rotation angles of the rotatable component 120 about the rotation axis 130. This aspect of the rotatable guidance 120 component differs significant from known devices in which an external rotatable component is rotatable about a rotation axis that is configured to lie within the patient anatomy, at a location corresponding to an internal anatomical feature.

In one example implementation, the rotation axis 130 may be located at the distal end 118 of the anchoring component 110, such that the rotation axis 130 lies within the plane of the distal surface 118. In another example embodiment, the rotation axis 130 may be located at a location that is proximal to the distal end 118 of the rotatable guidance component 120 (such that the rotation axis 130 passes through the distal region of the anchoring component. For example, this may be achieved by providing, at a location that is adjacent to the distal end of the anchoring component 118, a rotation pin 301 about which the rotatable guidance component 120 is confined to rotate.

Figure 1C:
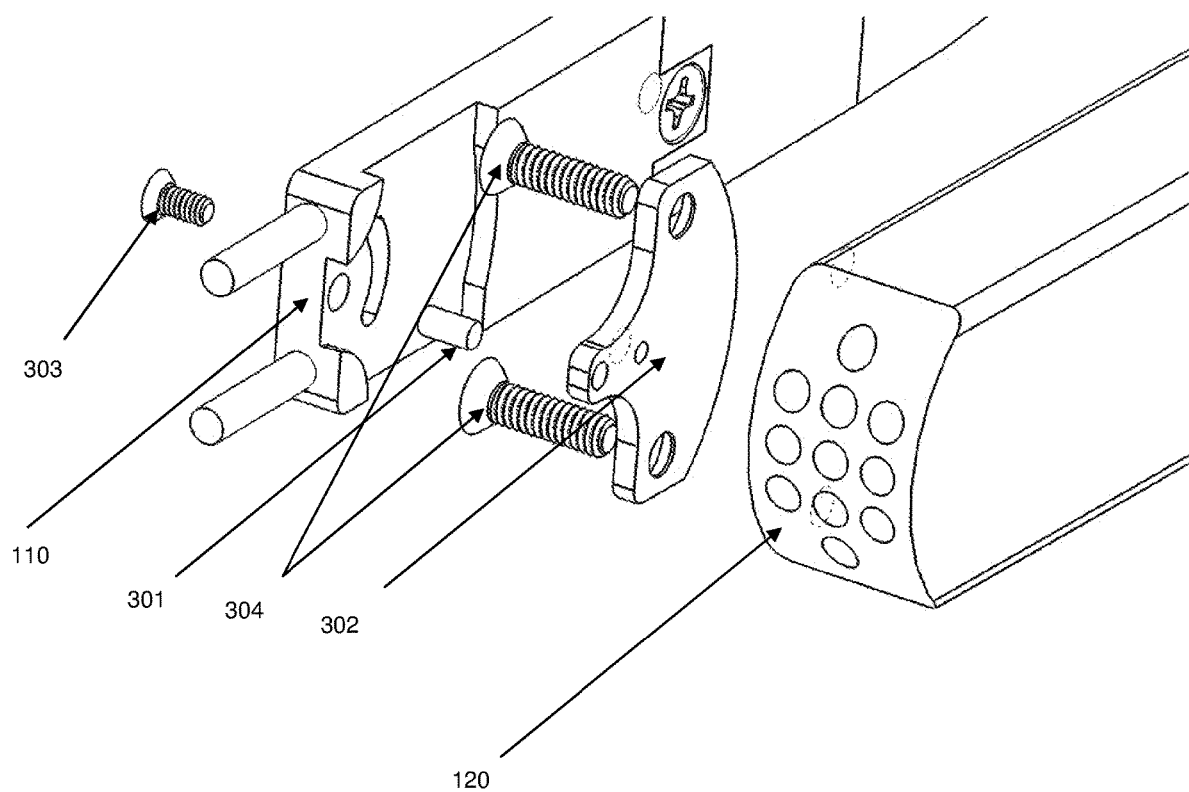
FIG. 1C shows a detailed view of the distal region of the positioning and alignment instrument.

An example of such a configuration is shown in FIG. 1C, where a rotation pin 301 is housed inside the anchoring component 110 to guide the rotatable guidance component 120 via a connecting plate 302. The connecting plate 302 is attached to the rotatable guidance component 120 and the anchoring component 110. The connection plate 302 is secured to the anchoring component 110 using a screw 303 and rigidly attached to the rotatable guidance component 120 with two or more screws 304.

Figure 1D:
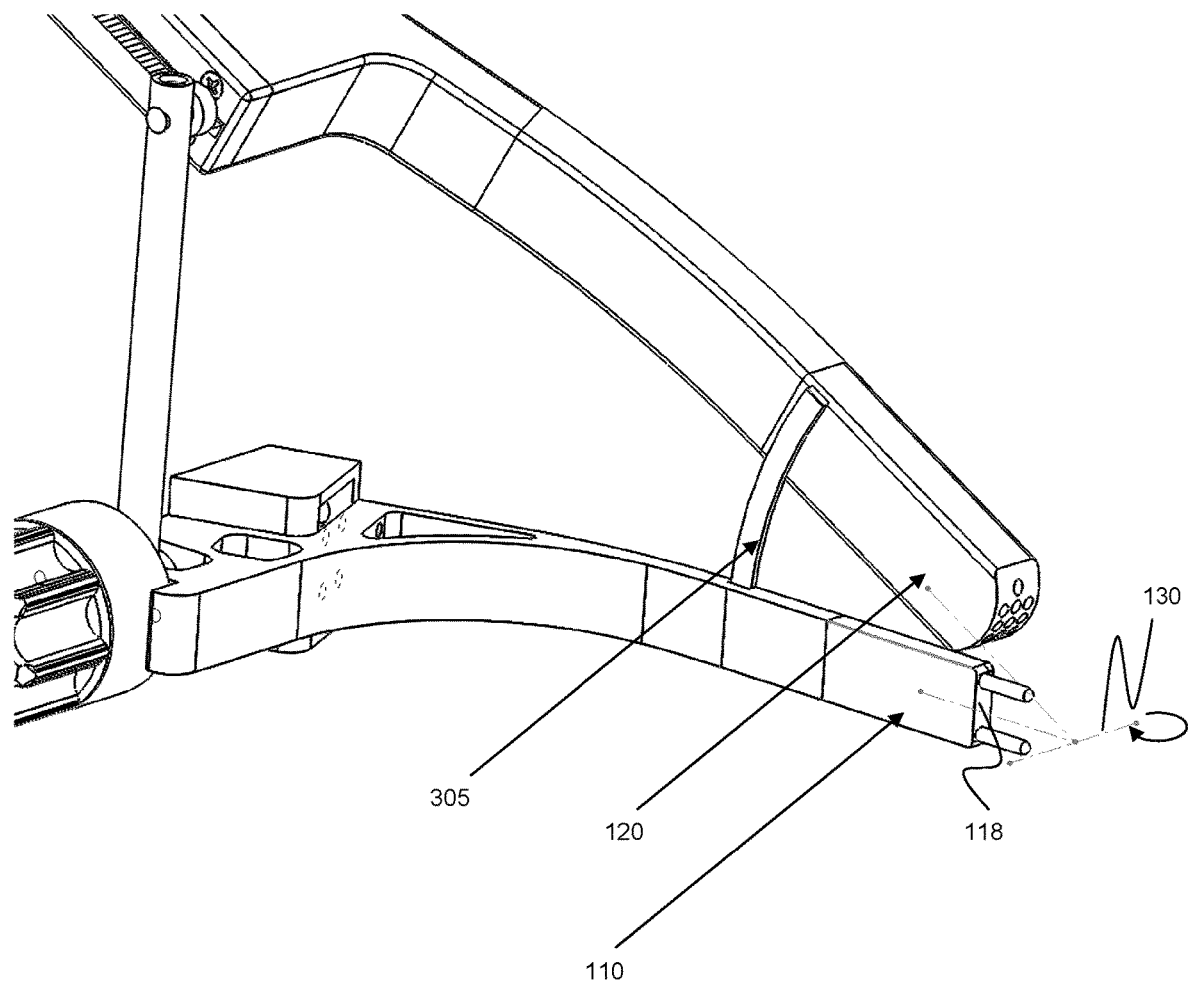
FIG. 1D illustrates an alternative embodiment in which the guidance component is rotatably supported by the anchoring component such that the rotation axis lies distalward relative to the distal end 118 of the anchoring component.

In yet another example embodiment, the anchoring component 110 and the rotatable guidance component 120 may be configured such that the rotation axis 130 lies distalward relative to the distal end 118 of the anchoring component 110. For example, such a configuration is shown in FIG. 1D, where a supporting mechanism 305 is attached to the rotatable guidance component 120 and the anchoring component 110.

The positioning and alignment instrument 100 may include a rotation actuation mechanism for actuating rotation of the rotatable guidance component 120. In the example implementation shown in FIGS. 1A and 1B, the rotation actuation mechanism is located proximal to a handle 135, where the handle forms or is attached or otherwise connected to a proximal portion of the anchoring component 110.

The rotation actuation mechanism may be positioned such that it is suitable for single-handed actuation by a user while holding the handle with a single hand. FIGS. 1A and 1B illustrate an example rotation actuation mechanism that includes a knob 150 that engages with a set screw 152 that is provided in a rotatable connection shaft 154, such that when the knob 150 is rotated, the connection shaft 154 is rotated.

Figure 1E:
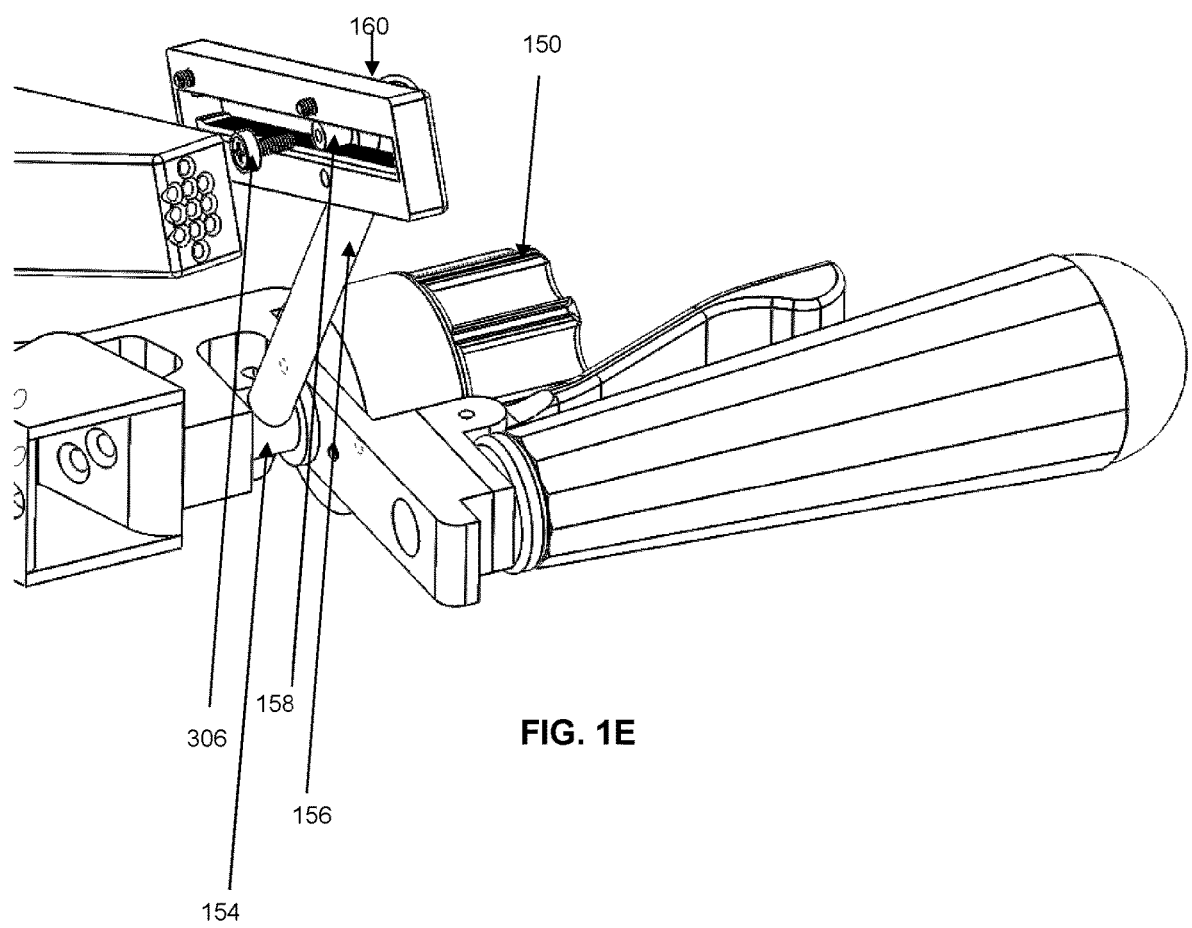
FIG. 1E shows a detailed assembly view of the rail that is provided in the proximal portion of the guidance component.

The rotation of the knob 150 produces corresponding rotation of the connection shaft 154, which in turn rotates linkage shaft 156, to which the connection shaft 154 is connected. The linkage shaft 156 extends in a distalward direction relative to the connection shaft 154, and a connection pin 158 extends from the linkage shaft 156 at or near its distal end. The connection pin 158 is received and secured with a screw 306 within a rail 160 provided in a proximal portion of the rotatable guidance component 120 as shown in assembly view in FIG. 1E. The rotatable guidance component 120, which is confined to rotate about the rotation axis 130 as described above and illustrated in FIG. 1C, thus rotates about the rotation axis 130 when the knob 150 is rotated, via the coupling of the rotational motion through the connection shaft 154, the linkage shaft 156, and the confined travel of the connection pin 158 within the rail 160. The proximal location of the knob 150 relative to the handle enables single-handed rotational actuation.

In some example embodiments, the rotatable guidance component 120 may be optionally and removably locked in a fixed angular configuration by a rotation locking mechanism, such that the rotatable guidance component 120 is only rotatable when the rotation locking mechanism is actuated by the operator. An example rotation locking mechanism is illustrated in FIGS. 1A and 1B. When the locking trigger 170 is not actuated by the operator, a first gear 162 formed in or attached to the knob 150 is biased, by a spring 164 and a set screw 166, to engage with a second gear 168 that is fixed relative to the anchoring component 110. When the operator applies a force to the trigger 170, the first gear 162 is disengaged from contact with the second gear, thus permitting rotation of the knob 150. This example locking mechanism is capable of single-handed actuation.

It will be understood that the rotation mechanism and the rotation actuation mechanism that are illustrated in FIGS. 1A and 1B are provided to illustrate merely one example implementation, and that a wide variety of alternative rotation mechanisms and rotation actuation mechanisms may be employed without departing from the intended scope of the present disclosure.

Examples of alternative rotation mechanisms and configurations include, but are not limited to a mechanism where the rotating knob 150 is placed perpendicular to its current configuration and a gear mechanism is used to transmit the rotational movement.

Examples of alternative rotation actuation mechanisms and configurations include, but are not limited to, (i) a motorized mechanism where a push of a button turns the motor in clockwise and/or counterclockwise directions which in turn rotates the connection shaft 154, and (ii) a direct rotation of the rotational guidance component 120.

Furthermore, examples of alternative rotation locking mechanisms include, but are not limited to, (i) a ratcheting mechanism where the movement of the rotatable knob 150 is constrained in clockwise and/or counterclockwise directions, and (ii) a magnetic mechanism where the attraction of opposite magnetic poles restricts the rotational movement of the connecting shaft 154.

Figure 1F:
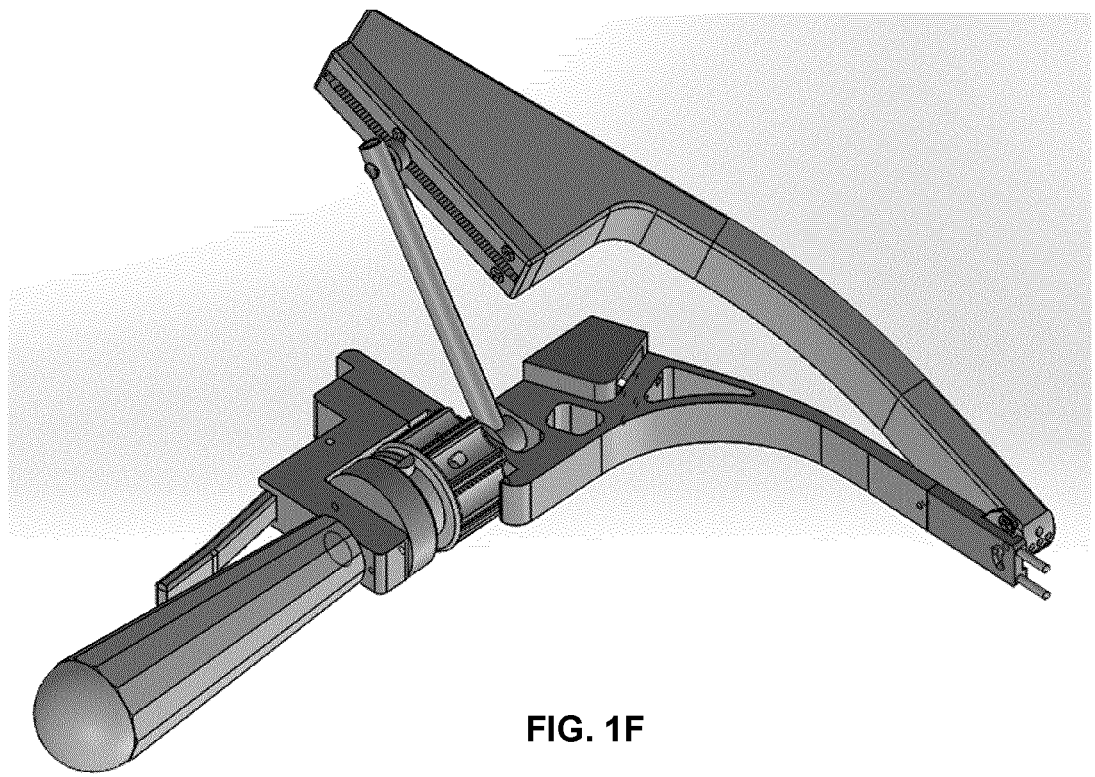
FIG. 1F shows an alternative implementation of the orientation of the handle.

FIG. 1F shows an alternative implementation of the anchoring component, where the handle, rotation knob, and locking mechanism are positioned in a different configuration than in the previous embodiments.

Figure 1G:
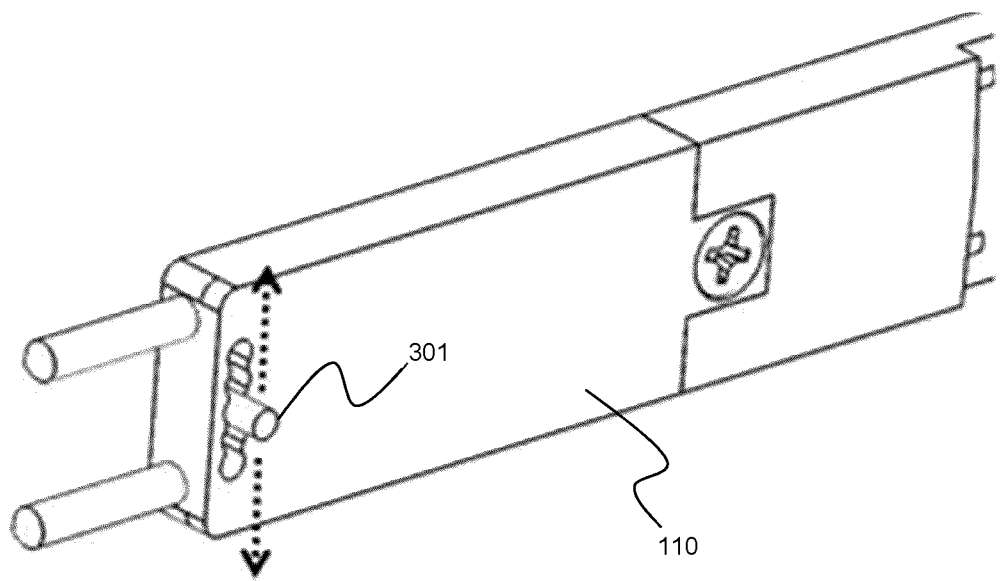
FIG. 1G shows a detailed view of the distal region of the anchoring component, illustrating an example embodiment in which the position of the rotation pin is adjustable relative to the anchoring component.

In some example embodiments, the guidance and alignment instrument may be further configured to permit one or more additional degrees of freedom in the alignment of the guidance component relative to the anchoring component. For example, as illustrated in FIG. 1G, the position of the rotation pin 301 may be adjustable relative to the anchoring component 110. Such an embodiment may permit lateral adjustment of the location of the rotation axis once the anchoring component 110 is anchored into bone. In other example embodiments, the rotation pin 301 may be adjustable in other directions, such as along the longitudinal direction of the anchoring component 110.

In order to anchor the anchoring component 110 into the bone, a force must be applied with sufficient magnitude in order to cause the anchoring protrusions to penetrate the bone surface and become embedded in the bone. This may be achieved by applying a force, such as with a hammer or other suitable tool, to a proximal surface of the anchoring component 110. In some example embodiments, a suitable proximal surface may be accessible regardless of the orientation of the rotational guidance component 120.

However, in the example implementation shown in FIGS. 1A and 1B, the proximal surface of the anchoring component 110 is substantially occluded by the rotational guidance component 120 when the rotational guidance component 120 is aligned with the anchoring component 110 (this aligned configuration is shown in FIG. 1B). Therefore, it may be necessary to rotate the rotatable guidance component 120 to a sufficiently large angle in order to provide access to a suitable proximal surface for delivering an impact force thereto. An example of such an orientation is shown in FIG. 1A, where the rotatable guidance component is rotated to a sufficiently large angle to provide access to proximal surfaces 172 and 174. This proximal region may be configured to present a single surface that is suitable for receiving an impact force from a tool such as a hammer.

In another example implementation, a force coupling tool may be employed to temporarily and removably contact the anchoring component 110, such that a force applied to a proximal surface of the force coupling tool is coupled to the anchoring component 110 via contact therewith. An example of such an embodiment is shown in FIGS. 2A-2C.

Figure 2A:
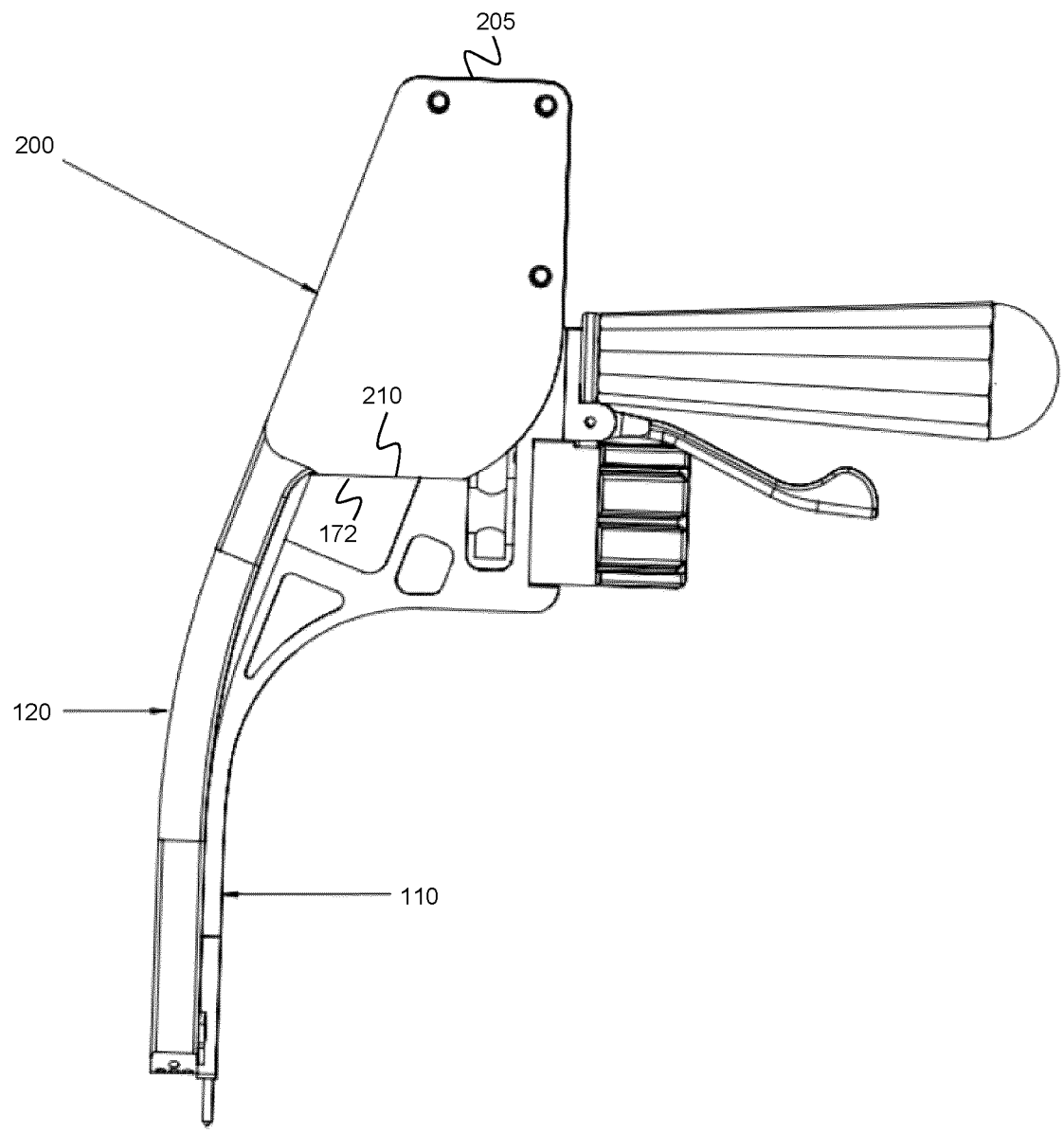
FIGS. 2A-2C show the use of an example force coupling tool for applying an impact force to drive the anchoring protrusions of the anchoring component into bone.

FIG. 2A shows an example embodiment in which the positioning and alignment instrument is contacted with a force coupling tool 200. The example force coupling tool slides overtop of the proximal portion of the anchoring component 110 (and, in this example case, the proximal portion of the rotatable guidance component 120). A distal surface 210 of the force coupling tool 200 abuts against the proximal surface 172 of the anchoring component 110 (a similar abutment occurs on the opposite side of the device with proximal surface 174). This abutment provides contact such the application of a force (e.g. an impact force) to the proximal surface 205 of the force coupling tool 200 is coupled (e.g. communicated; transferred) to the anchoring component 110, and is thereby also transferred to the anchoring protrusions 115. The proximal surfaces 172 and 174 (or a single proximal surface) of the anchoring component may be established by a separate component that is attached to the anchoring component 110, or may be integrally formed as surfaces of the anchoring component 110.

Figure 2B:
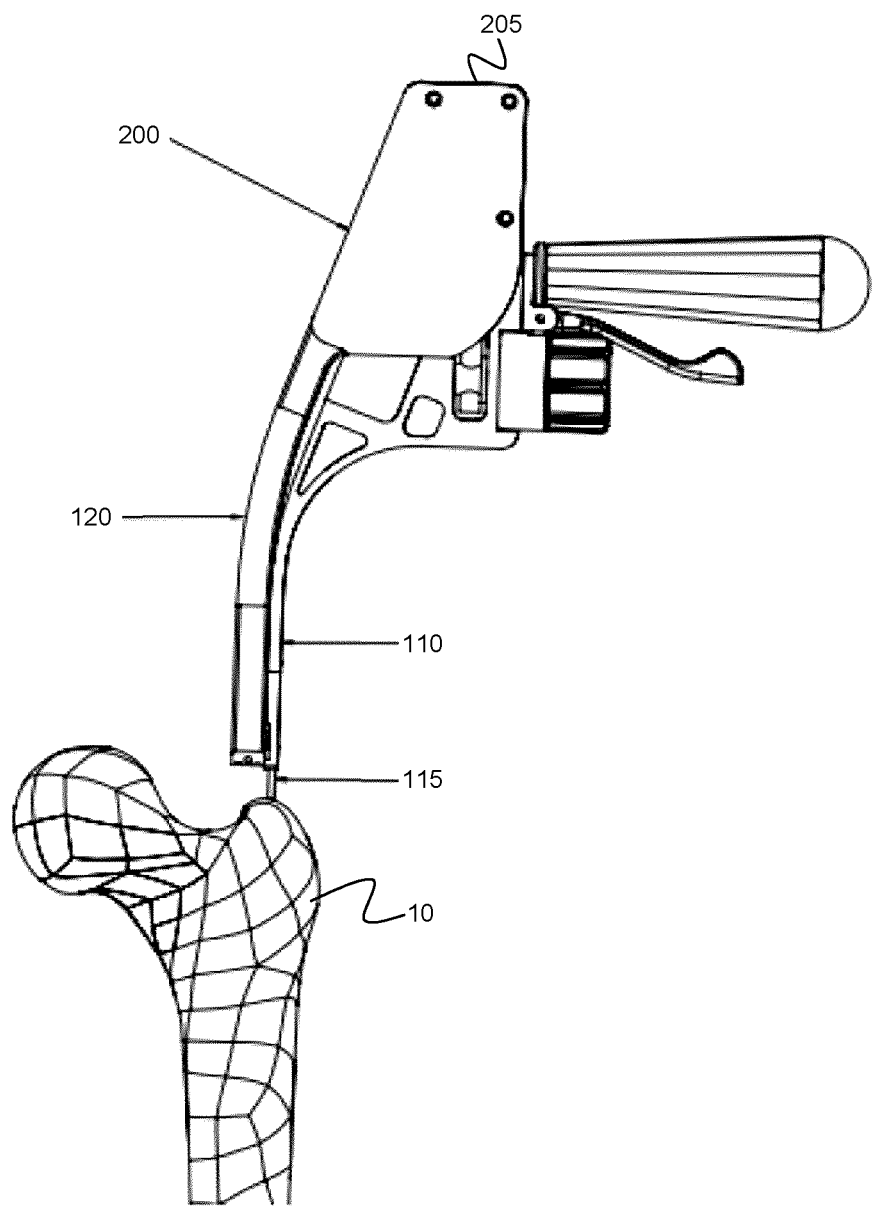

FIG. 2B shows the positioning and alignment instrument, having the force coupling tool 200 provided thereon (e.g. contacted therewith or attached thereto), with the anchoring protrusions 115 positioned at a suitable location for insertion into the bone 10. Upon the delivery of a suitable force to the proximal surface 205 of the force coupling tool 200, as shown in FIG. 2C, the anchoring protrusions 118 are delivered into and anchored within the bone 10, such that the distal surface 118 of the anchoring component 110 lies adjacent to the bone surface. The configuration shown in the present example embodiment, in which the force coupling tool slides over proximal portions of both the anchoring component 110 and the rotational guidance component 120, may be beneficial in preventing rotational movement of the rotational guidance component during anchoring and protecting various components (such as the rotational guidance component 120) from impact or the application of undue stress.

Figure 2C:
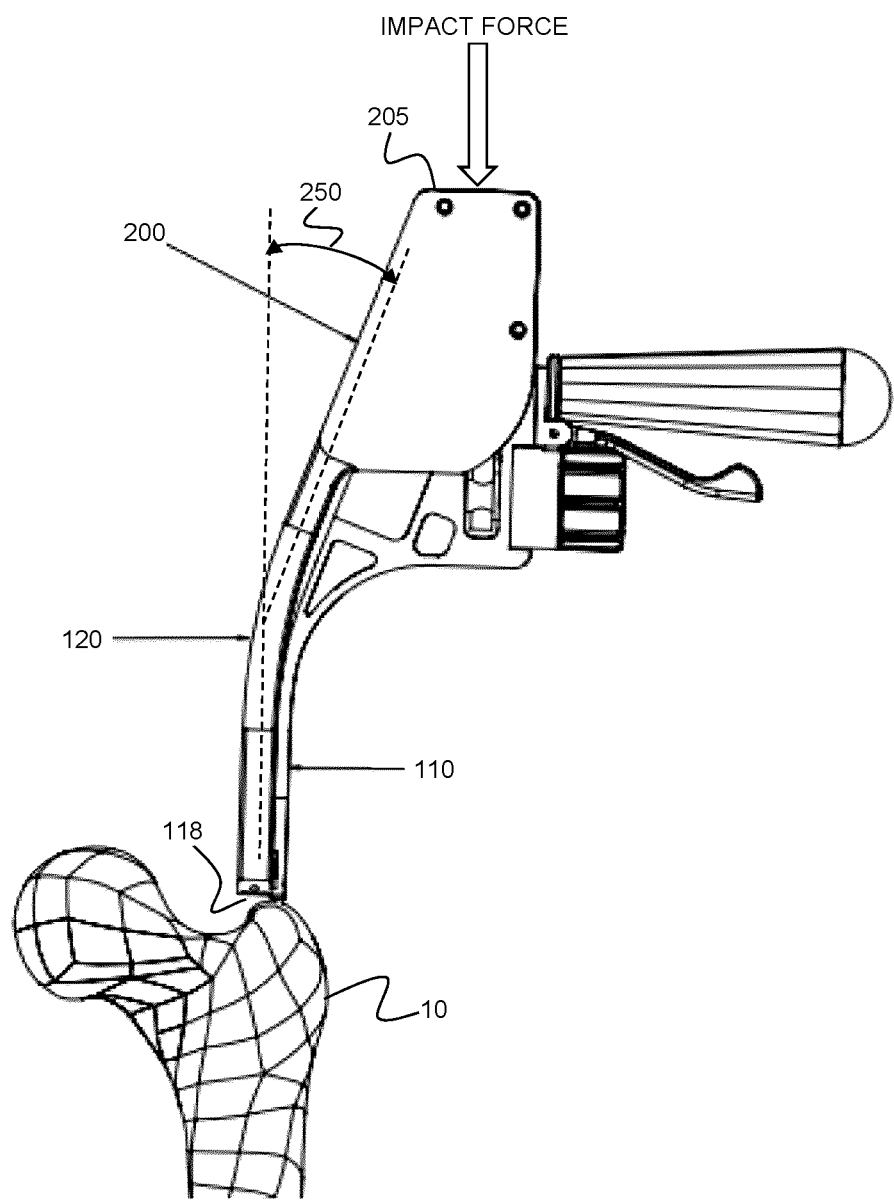

It will be understood that the force coupling tool shown in FIGS. 2A-C provides but one non-limiting example of a mechanism for providing a force sufficient to deliver the anchoring protrusions into bone. In other example embodiments, the force coupling tool may be configured for delivery of the anchoring protrusions into the bone in the absence of an impact force.

Figure 2D:
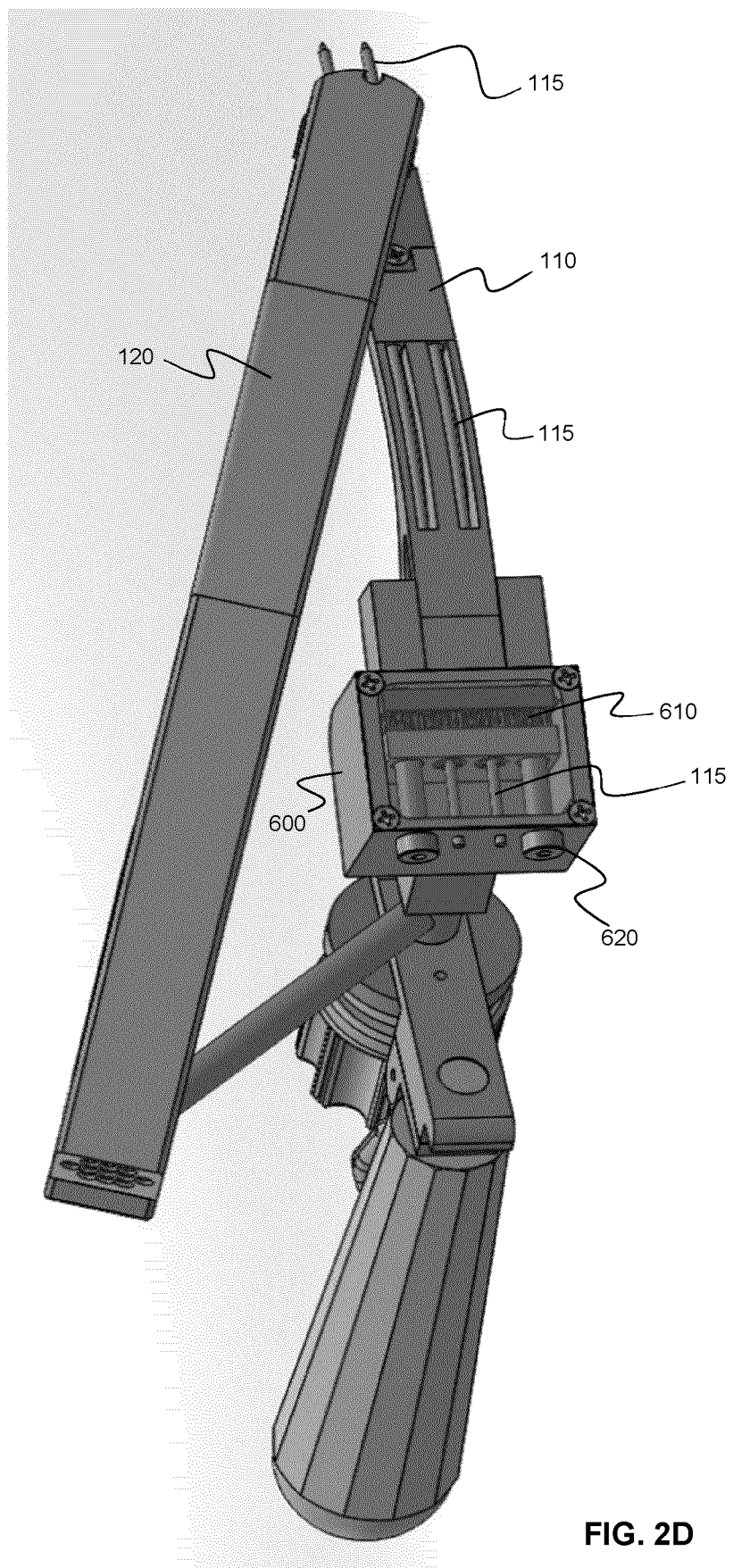
FIGS. 2D-2E illustrate the use of an alternative force coupling tool that is configured to drill the anchoring protrusions into bone.
Figure 2E:
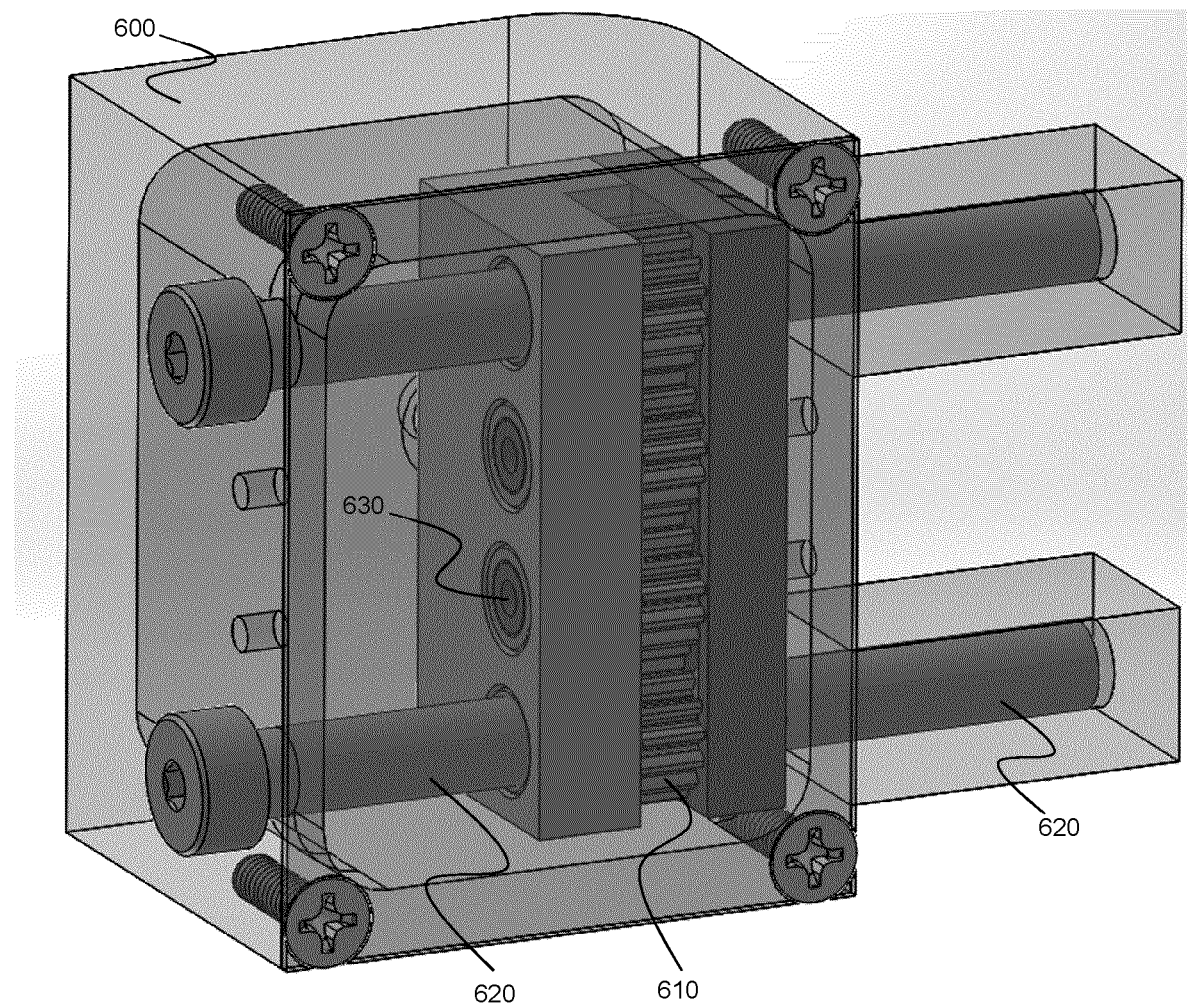

Referring now to FIGS. 2D and 2E, an example embodiment is illustrated in which a gearbox 600 is employed to rotate the anchoring protrusions 115, thereby facilitating a drilling action of the anchoring protrusions 115 into bone. According to this alternative example embodiment, the anchoring of the device may be achieved by drilling the anchoring protrusions 115 (as opposed to hammering them) into the bone.

This alternative modality for anchoring the device may be advantageous, for example, in the case of a proximal femoral fracture. In such a case, the instability of the proximal fragment can limit the ability of the anchoring protrusions to be effectively hammered into the bone. The present example embodiment avoids the need to deliver the anchoring protrusions into bone under an impact force by employing a gearbox to drill the one or more anchoring pins into the greater trochanter of the femur, thereby facilitating the securing of the device to an unstable bony fragment.

As shown in FIGS. 2D and 2E, the force coupling tool includes a gearbox 600 that contacts a proximal portion of the anchoring component 110, optionally being fixed or removably attached to the anchoring component 110. The gearbox 600 houses a gear train 610 configured to rotate the one or more anchoring protrusions of the device. A proximal portion of the gearbox includes at least one screw 620 that is configured to actuate the gear train 610, such that when the screw 610 is rotated during application of a longitudinal force thereto, the longitudinal force is coupled to the anchoring protrusions during rotation, where the rotation facilitates the drilling of the anchoring protrusions into bone.

In the example embodiment illustrated in FIGS. 2D and 2E, the anchoring protrusions are provided as elongate flexible pins 115 that extend through or along, and are supported by, the anchoring component 110. The pins 115 are shown extending from a distal end of the anchoring component 110 to form the anchoring protrusions. A proximal portion of each pin 115 extends from the proximal portion of the anchoring component 110 and is received within a respective pin-receiving gear of the gear train 610, such that actuation of the gear train produces concomitant rotation of the pins 115.

During use, the surgeon uses a drill to rotate the screw 620, thus actuating the gear train 610 and producing rotation of the pins 115. The gearbox 600 translates the rotation to the other gears, and both pins 115 rotate simultaneously. As the surgeon advances the screw 620, the device moves forward, thereby providing a simultaneous advancing force and rotational movement to drive the pins 115 into the bone. This enables a rapid effective single step for attachment of the device to the bone. The axial force applied to the screw 620 during drilling causes the whole mechanism to advance toward the bone. The elongated shape of the gearbox 600 enables the screws 620 to move in this axial direction without risk of engaging the patient's skin or soft tissues.

In the example embodiment shown in FIGS. 2D and 2E, two screws (top and bottom screws) are provided on either side of the gear train 610, where each screw is configured to actuate the gear train 610, thus allowing the surgeon to select a screw that is most easily accessible (e.g. depending on the side (left or right femur) that the surgeon is operating on). It is also noted that the screws 620 sit offset from the guidance component 120, thereby allowing indirect access to the pins 115, in order to enable access despite the presence of the guidance component 120.

Although the present example embodiment illustrates a device in which pins 115 are rotated by the gearbox 600, it will be understood that the pins 115 can be replaced with screws according to other example embodiments. For example, in one example implementation, the gearbox 600 may be configured to rotationally drive one or more flexible drill bits supported by the device. The flexible drill bits may be removable and replaceable, thereby enabling the use of different tip attachments of variable shaft diameter/shape at the device/bone interface.

As shown in FIGS. 1A, 1B, and in particular, FIG. 2C, the positioning and alignment instrument may be shaped such that a proximal portion thereof deflects, bends, curves, or otherwise angles outwardly relative to a longitudinal axis (a device guidance axis) associated with a distal region of the rotatable guidance component 120. This geometrical configuration may be useful, beneficial or important in providing the surgeon suitable ergonomic manipulation of the positioning and alignment device during use. For example, when the position and alignment instrument shown in FIG. 2C is employed during an intramedullary nailing procedure, the outward deflection of the proximal region of the instrument (as shown at 250) enables the surgeon to apply an impact force to a proximal region of the instrument without risk, or with reduced risk, of contacting the patient. The deflected configuration also positions the handheld portion of the device further away from the subject than in a collinear (straight) configuration, which may provide for a more efficient and safe surgical procedure. In some example embodiments, at least a portion of the positioning and alignment instrument is deflected (angled) outwardly relative to the distal longitudinal axis by an angle between 0 and 45 degrees. It will be understood that the shape of the instrument may vary depending on clinical application and/or anatomical side of the subject. For example, the instrument may have different shapes for operating on a left or right limb (e.g. for optimal positioning of the handle).

Although the example positioning and alignment instruments described herein may be employed for a wide variety of applications and medical procedures, an example method of employing such an instrument during an intramedullary nailing procedure is described below. It will be understood that the methods below are merely provided as being illustrative of the application of the example positioning and alignment instrument embodiments disclosed herein.

FIGS. 3A-3E illustrate the cumbersome and iterative nature of a conventional intramedullary (IM) nailing procedure involving the alignment of a Kirschner wire (K-wire), where the entry point location and orientation both have a significant impact on the overall outcome of the IM nailing procedure. During a conventional IM nailing procedure, fluoroscopy images are obtained in the AP direction (through the coronal plane).

Once adequate images with respect to entry point location and K-wire orientation are acquired in the AP direction (see FIG. 3A), errors in sagittal placement must be addressed. If the sagittal entry point location is correct but the lateral orientation is incorrect (FIG. 3B), the surgeon must alter the anterior-posterior angle of entry of the K-wire about the identified entry location (ensuring no displacement of the K-wire tip from the entry site). If the sagittal entry point location is incorrect but the orientation is correct (FIG. 3C), the surgeon must adjust the anterior-posterior translation along the sagittal plane without any change in sagittal angulation of the K-wire. If the sagittal entry point location and orientation are both incorrect (FIG. 3D), then the surgeon must first readjust the entry location in the sagittal plane. Once the correct new entry location is verified with lateral fluoroscopy, the surgeon must then readjust the K-wire orientation in the sagittal plane to ensure parallelism in access to the IM canal (FIG. 3E); following this step, the surgeon needs to recheck the AP view to ensure that both the coronal plane entry point and wire orientation are acceptable. As can be understood with reference to FIGS. 3A-3E, multiple cycles of anterior-posterior (AP) and lateral imaging may be required to confirm the optimal entry point positioning. This unpredictable repetition of activities, can be time-consuming, frustrating, costly, and can impact patient outcomes.

Referring now to FIGS. 4, and 5A-5C an example method of aligning a device during medical procedure involving guide wire insertion during a femoral intramedullary (IM) nailing procedure is described. Unlike the conventional iterative and repetitive method of K-wire positioning and alignment described above, the example method described below employs the fixation of the anchoring component and relative rotation of the rotatable guide component. This fixation and controlled relative rotation provides a method that is deterministic and thus avoids the iterative trial-and-error nature of the conventional method.

Figure 4:
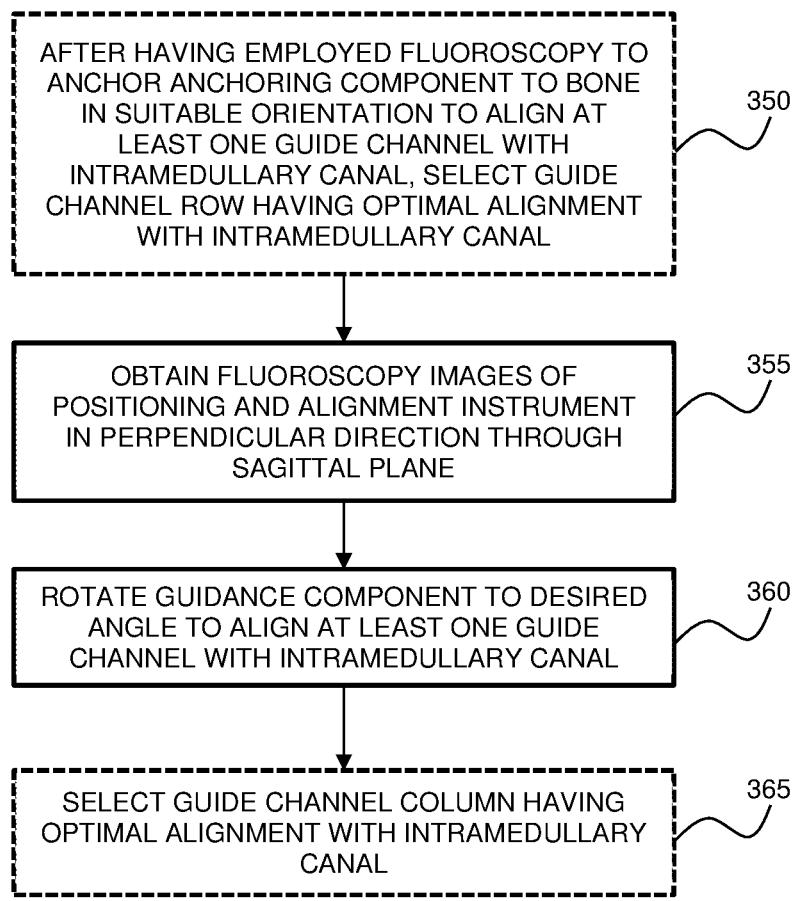
FIG. 4 is a flow chart illustrating an example method in which a position and alignment instrument is employed a medical procedure involving the introduction of a device into bone.
Figure 5A:
FIGS. 5A-5C show fluoroscopy images of the positioning and alignment instrument during various steps of the method illustrated in FIG. 4.
Figure 5B:
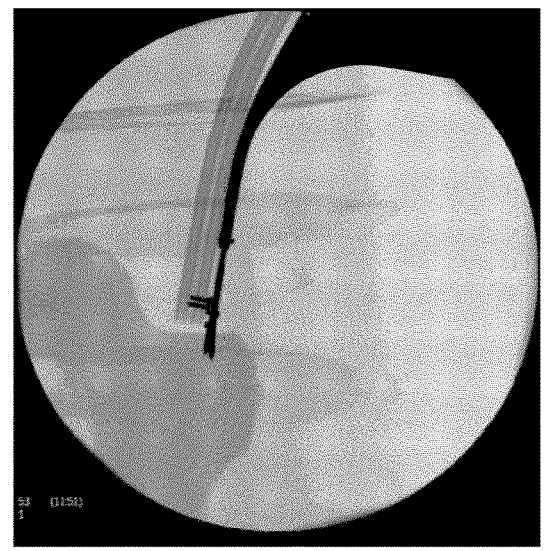
Figure 5C:

FIG. 4 shows a flow chart illustrating the steps in the example fluoroscopy-based method, and FIGS. 5A-C show images of an example positioning and alignment instrument during steps of the procedure. It is noted that the following method steps shown in FIG. 4 are performed after having inserted the guidance instrument into the bone, and that the following steps do not involve the step of the insertion of the device into the bone, and rather recite steps for aligning the device for subsequent insertion into the bone. The illustrated method steps therefore do not pertain to a surgical intervention per se.

Prior to performing the method steps shown in FIG. 4, the positioning and alignment instrument is initially placed, under fluoroscopic image guidance, at the approximate IM nailing entry point location, which, in the present non-limiting example, resides at the piriformis fossa or greater trochanter. Anterior-posterior (AP) images are employed to align the positioning and alignment instrument such that at least one device guide channel of the guidance component is aligned with the intramedullary canal of the femur, as shown in FIG. 5A. Once this initial two-dimensional alignment is satisfactory, the instrument is subjected to a force (as shown in FIG. 2C) to anchor the anchoring protrusions into the greater trochanter of the femur. FIG. 5B shows an AP image showing the positioning and alignment instrument with the anchoring component anchored to the bone.

Figure 5D:
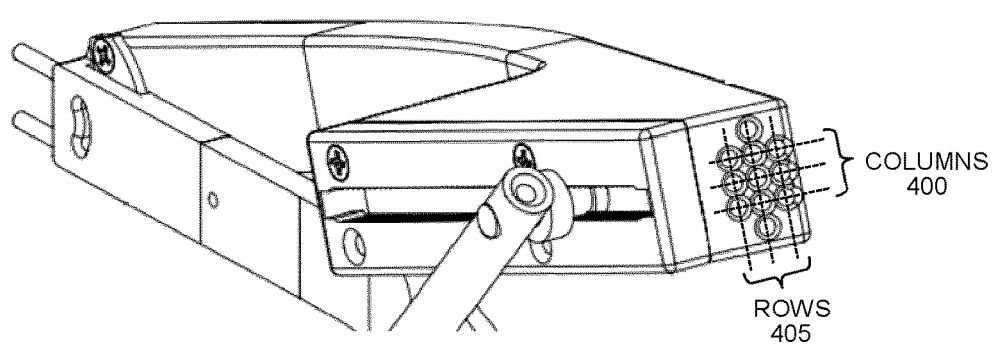
FIG. 5D shows the two-dimensional array of device guide channels visible at the proximal end of the rotatable guidance component.

As shown in FIG. 5D, the example positioning and guidance instrument includes a two-dimensional array of device guide channels, including a plurality of rows 400 (perpendicular to the rotation axis at the distal end of the rotational guide component) and a plurality of columns 405 (parallel to the rotation axis at the distal end of the rotational guide component). According to such an instrument configuration, when multiple rows of device guide channels are visible in the AP images, the AP image may be employed to select a guide channel row that is best (optimally) aligned with the intramedullary canal, as shown at step 350 in FIG. 4. It will be understood that this step may optionally be performed in cases in which the guidance component includes a plurality of rows of device guide channels that are observable in the AP image (the optional nature of this step is indicated by the dashed flow chart element 350 in FIG. 4). In various example embodiments, the guidance component may only include a single device guide channel, a single row of device guide channels, a single column of device guide channels, or a two-dimensional array of rows and columns of device guide channels.

Figure 6:
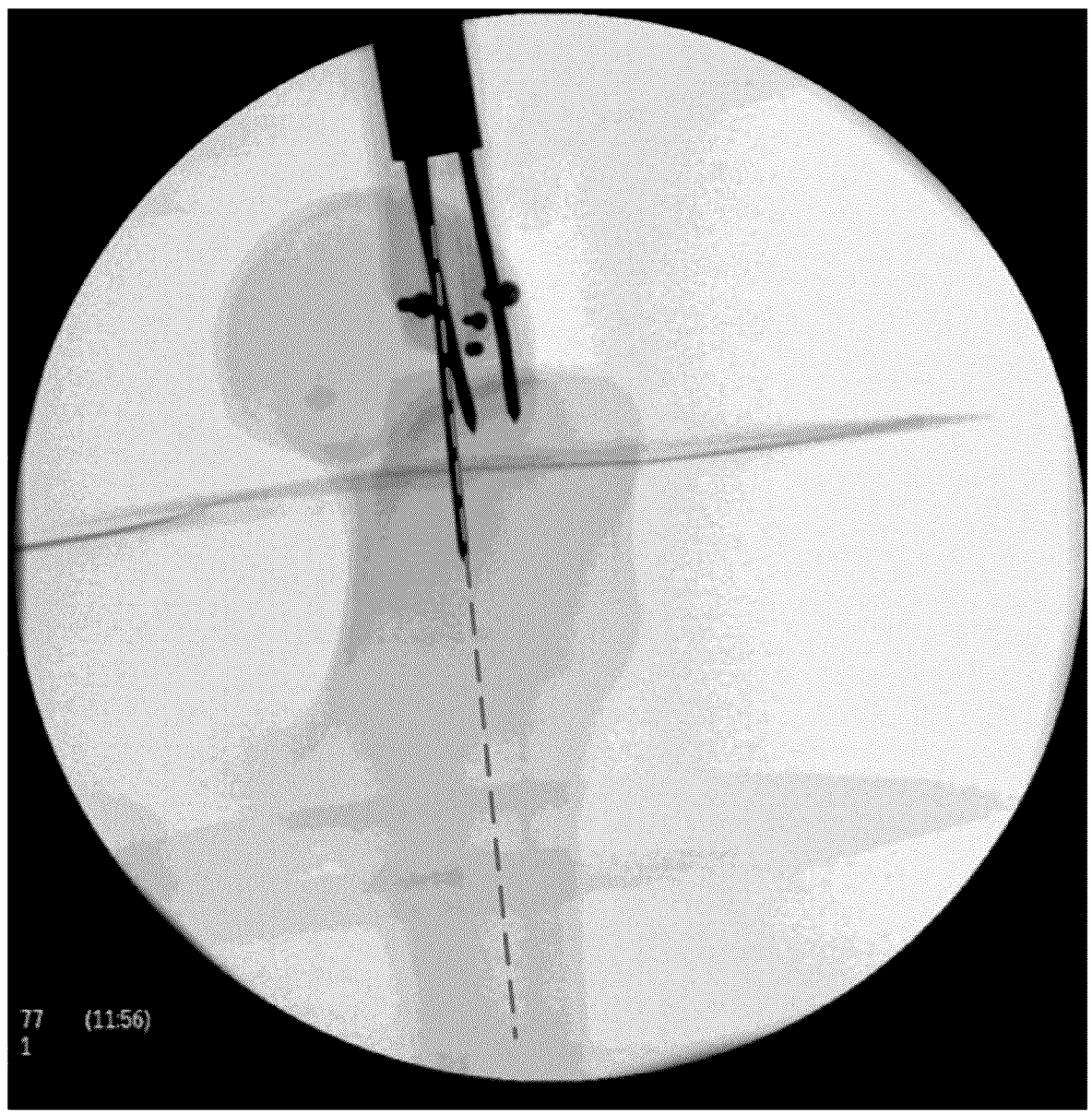
FIG. 6 shows a fluoroscopy image showing the introduction of a Kirschner wire into bone following the positioning and alignment of the Kirschner wire using an example positioning and alignment instrument.

As shown in step 355 of FIG. 4, one or more subsequent lateral (or oblique-lateral) images (e.g. images in a perpendicular direction that includes the sagittal plane) are then obtained to identify the correct three-dimensional trajectory for accessing the intramedullary canal. The guidance component is then rotated relative to the anchoring component in order to align the guidance component with the intramedullary canal, as shown at step 360. Such a configuration is shown in FIG. 6, where the rotational guidance component has been rotationally aligned such that the K-wire is axially aligned with the intramedullary canal upon insertion therein.

In the event that the position and alignment instrument includes multiple columns of device guide channels (as in FIG. 5D), the device guide channels visible in the lateral image may be employed, as shown in step 365 to select the column (while maintain the selection of the row, if performed in step 350) that provides the optimal alignment of the device guide channel with the intramedullary canal.

As described above with reference to FIGS. 1A and 1B, the positioning and alignment instrument may include a rotation actuation mechanism, and the rotation actuation mechanism may be located proximal to, or adjacent to, a handle portion of the anchoring component, such that the rotation actuation mechanism can be actuated single-handedly while holding the handle.

Unlike the conventional method described with reference to FIGS. 3A-3E, the present example method enables deterministic positioning and alignment of a device without requiring an iterative trial-and-error based approach. This is achieved by the fixation of the anchoring component during the initial collection of images, and the subsequent rotation of the guidance component during the acquisition of images from a perpendicular direction, where the guidance component is rotated in an arc that is fixed relative to the anchoring component, such that the initial alignment in the first direction is preserved and maintained when aligning the remainder of the rotational guidance component in the second direction.

Having obtained alignment of the guidance component, using the aforementioned direct and deterministic method, the device may be subsequently guided by the selected device guide channel (i.e. along the selected row and column) for controlled insertion into the bone.

It will understood that the specific implementation shown in FIGS. 1A and 1B is provided to illustrate one example and non-limiting configuration of a positioning and guidance instrument, and other configurations may be employed for other clinical applications. For example, in other example implementations, the device channel guides 122 need not extend to a distal location that is adjacent to the distal end 118 of the anchoring component 110.

In the various examples embodiments described herein, the device received within the device guide channel is a K-wire. However, it will be understand that a K-wire is disclosed as a non-limiting example of a broad class of devices. Accordingly, the term "device", as used herein, refers generally to any number of implantable devices, materials and instruments suitable for bone treatment and/or repair. For example, the device may be an implantable device, an insertion tool, a drill bit, an injection needle, a catheter, or any other surgical instrument.

Figure 9:
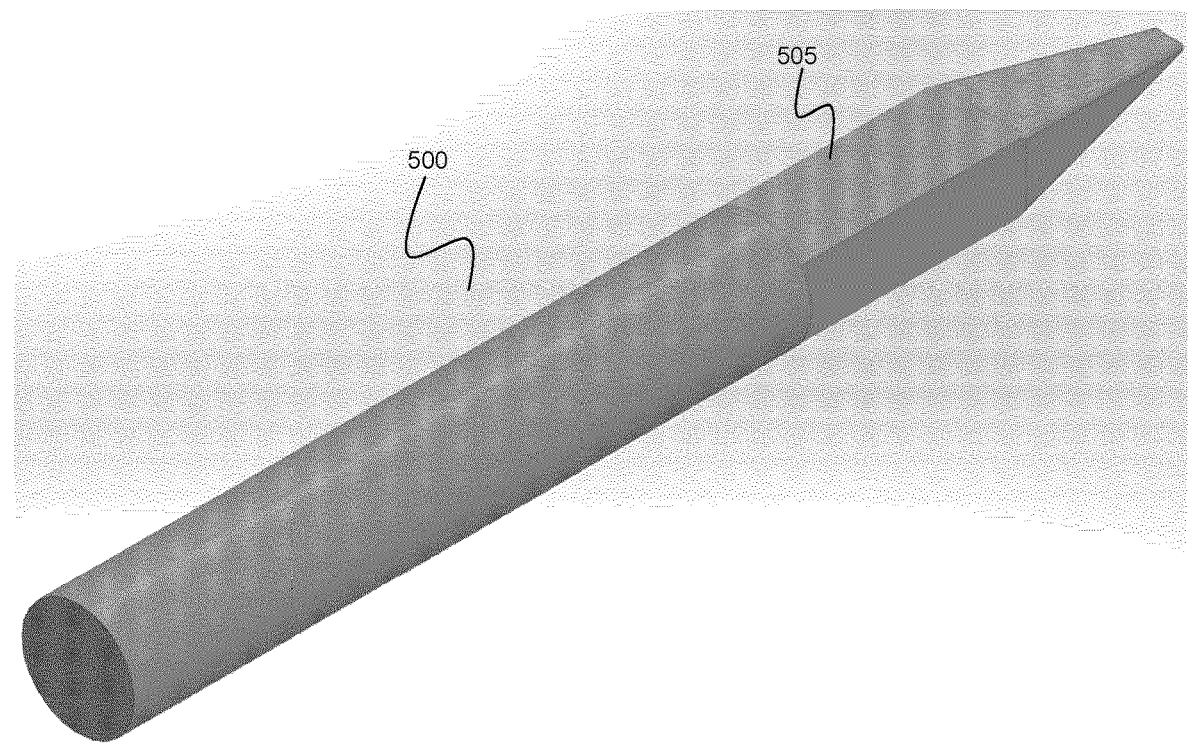
FIG. 9 shows an example alternative configuration of an anchoring protrusion.

While the positioning and alignment device illustrated in FIGS. 1A and 1B employs two anchoring protrusions, it will be understood that this specific configuration provides merely one example implementation, and that in general the anchoring component may have one or more anchoring protrusions, provided that the one or more anchoring protrusions are suitable for anchoring the anchoring component in a fixed position and fixed orientation. For example, FIG. 9 illustrates an example implementation of a single anchoring component 500 having a rectangular elongate segment 505 that enforces a fixed position and orientation when embedded in bone.

Although the preceding example embodiments involve intramedullary nailing procedures, it will be understood that the embodiments of the present disclosure may be applied to, or adapted to, a wide variety of surgical procedures, in which tool guide channels are aligned to internal anatomical or function features, or to features associated with embedded medical devices.

Figure 7:
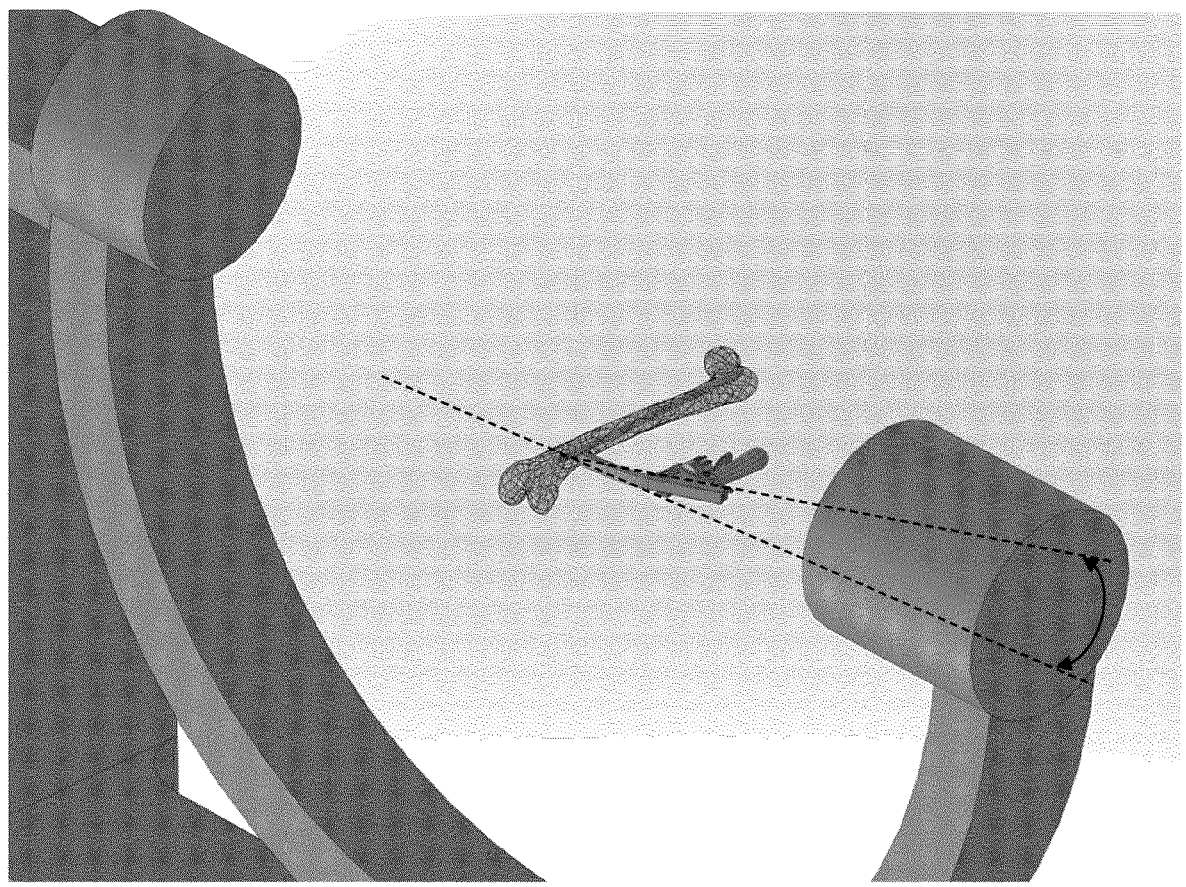
FIG. 7 shows the use of an example positioning and alignment instrument during the insertion of a locking screw into the distal end of an intramedullary rod during an intramedullary nailing procedure.
Figure 8:
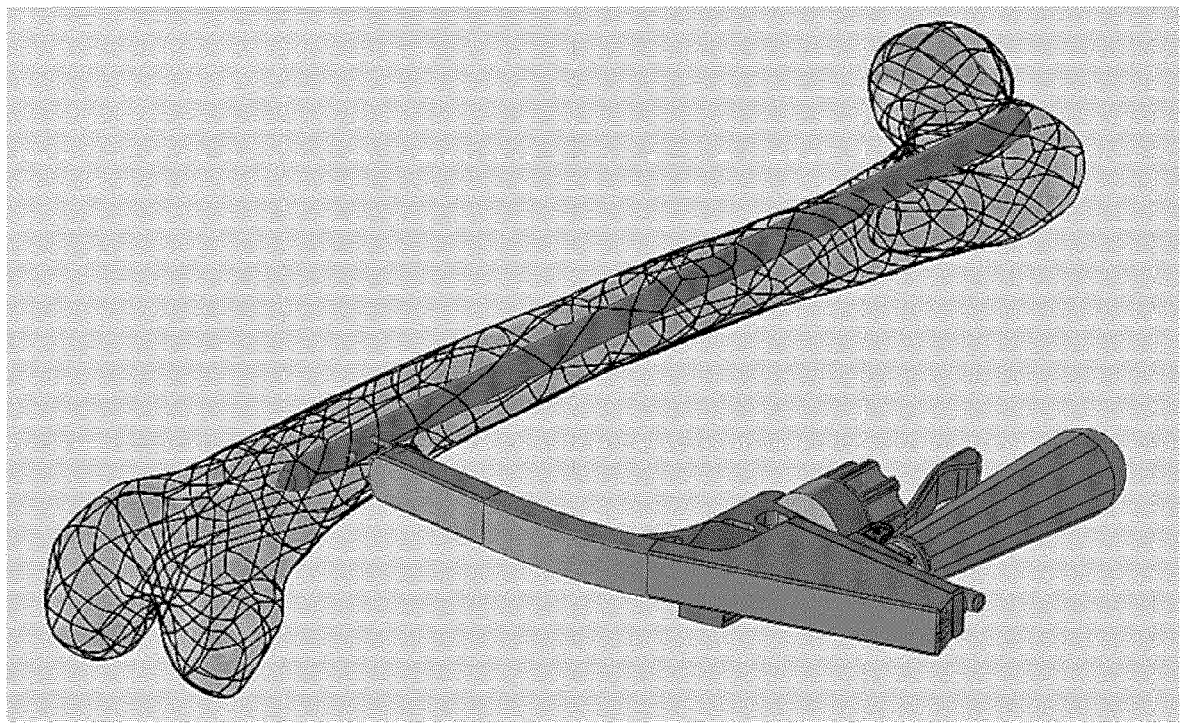
FIG. 8 shows an expanded view relative to FIG. 7, showing the orientation of the C-arm relative to the example positioning and alignment instrument.

For example, as shown in FIGS. 7 and 8, the positioning and alignment device may be employed to select a suitable position and orientation of a drill bit that is employed to drill an initial hole to guide the subsequent insertion of a locking screw into the distal region of an IM nail. Once the distal nail hole is seen as a circle under fluoroscopy and an incision is made, the device can be inserted into the bone. As shown in FIG. 7, the curvature of the rotatable guidance component is beneficial to reducing both the amount of the position and alignment instrument that lies within the path of the fluoroscopy beam and potential radiation exposure to the surgeon's hands. Once a correct guide channel is selected, a flexible drill bit can be advanced to make an initial hole for the subsequent insertion of a locking screw. This eliminates the need for a radiolucent drill or repeated assessments of the drill bit if a free hand technique is utilized. The positioning and alignment device of the aforementioned embodiments could also be utilized, for example, in prophylactic femoral, tibial or humeral nailing, or, for example, any other surgery that involves insertion of a surgical instrument into bone under fluoroscopic guidance.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A positioning and alignment instrument for guiding insertion of a device into bone, the positioning and alignment instrument comprising:

an anchoring component comprising a proximal portion and a distal portion, wherein said proximal portion comprises a handle, and wherein one or more anchoring protrusions extend from a distal end of said distal portion for anchoring said anchoring component into the bone, such that a position and an orientation of said anchoring component is fixed relative to the bone when said anchoring component is anchored to the bone; and a guidance component mechanically supported by said anchoring component, said guidance component comprising a device guide channel for receiving the device and guiding the device towards an insertion location adjacent to the distal end of said distal portion of said anchoring component, wherein said guidance component is rotatable relative to said anchoring component about a rotation axis that is located adjacent to the distal end of said anchoring component, such that the insertion location remains adjacent to the distal end of said distal portion of said anchoring component under rotation of said guidance component; and a rotation actuation mechanism for actuating rotation of said guidance component to vary an angle between said distal portion of said anchoring component and a distal portion of said device guide channel of said guidance component.

2. The positioning and alignment instrument according to claim 1 wherein said rotation actuation mechanism is located proximal to said handle such that said rotation actuation mechanism is capable of being actuated by a first hand of a user while holding said handle with the first hand, in the absence of use of a second hand.

3. The positioning and alignment instrument according to claim 2 wherein said rotation actuation mechanism is configured to be capable of actuation a thumb of the first hand while holding said handle with the first hand.

4. The positioning and alignment instrument according to claim 3 wherein said rotation actuation mechanism comprises a rotatable knob that is adjacent to said handle for actuation by the thumb.

5. The positioning and alignment instrument according to claim 2 further comprising a rotation locking mechanism for locking a rotation angle of said guidance component.

6. The positioning and alignment instrument according to claim 5 wherein said rotation locking mechanism is located proximal to said handle such that said rotation locking mechanism is capable of being actuated by the user while holding said handle with the first hand in the absence of use of the second hand.

7. The positioning and alignment instrument according to claim 1 wherein said guidance component comprises a slot having a slot axis that is parallel to said distal portion of said device guide channel, wherein said positioning and alignment instrument further comprises a linkage having a first end that is pivotally coupled to said proximal portion of said anchoring component, and a second end comprising a pin, wherein said pin is received in said slot.

8. The positioning and alignment instrument according to claim 1 wherein said guidance component is rotatably supported relative to said anchoring component such that said rotation axis is within 5 mm of the distal end of said anchoring component.

9. The positioning and alignment instrument according to claim 1 wherein said guidance component is rotatably supported relative to said anchoring component such that said rotation axis is within 2 mm of the distal end of said anchoring component.

10. The positioning and alignment instrument according to claim 1 wherein the distal portion of said device guide channel is aligned along a device guidance axis, and wherein a proximal portion of said device guide channel deflects outwardly relative to said device guidance axis toward said handle.

11. The positioning and alignment instrument according to claim 10 wherein said proximal portion is deflected outwardly at an angle of 0 to 30 degrees relative to said device guidance axis.

12. The positioning and alignment instrument according to claim 1 wherein said distal portion of said anchoring component has a rectangular cross-section, wherein a long axis of said rectangular cross-section is perpendicular to the rotation axis and wherein said one or more anchoring protrusions extend from the distal end of said anchoring component.

13. The positioning and alignment instrument according to claim 1 wherein said proximal portion comprises a proximal impact receiving surface suitably oriented to receive an impact for driving said one or more anchoring protrusions into the bone.

14. The positioning and alignment instrument according to claim 1 further comprising a force coupling tool configured to contact said anchoring component and drive said one or more anchoring protrusions into bone upon the application of a force thereto.

15. The positioning and alignment instrument according to claim 14 wherein said force coupling tool is configured to drive said one or more anchoring protrusions into bone when an impact force is applied thereto.

16. The position and alignment instrument according to claim 15 wherein said force coupling tool comprises a distal surface suitable for contacting said anchoring component, and wherein said force coupling tool comprises a proximal surface suitable for receiving an impact, such that when said force coupling tool is contacted with said anchoring component and an impact force is delivered to said proximal surface of said force coupling tool, the impact force is coupled through said force coupling tool to said anchoring component for driving said one or more anchoring protrusions into bone.

17. The positioning and alignment instrument according to claim 14 wherein said force coupling tool is configured to rotate said one or more anchoring protrusions while said one or more anchoring protrusions are driven into bone.

18. The position and alignment instrument according to claim 17 wherein said force coupling tool comprises a gearbox contacting a proximal portion of said anchoring component, wherein said gearbox houses a gear train configured to rotate said one or more anchoring protrusions;

wherein a proximal portion of said gearbox comprises a screw that is configured to actuate said gear train, such that when said screw is rotated during application of a longitudinal force thereto, the longitudinal force is coupled to said one or more anchoring protrusions during rotation thereof for driving said one or more anchoring protrusions into bone.

19. The position and alignment instrument according to claim 18 wherein said anchoring component supports one or more rotatable pins extending longitudinally therethrough, and wherein said one or more rotatable pins extend from a distal end of said anchoring component to respectively form said one or more anchoring protrusions; and wherein a proximal portion of each pin of said one or more rotatable pins extends from the proximal portion of said anchoring component and is received within a respective pin-receiving gear of said gear train, such that actuation of said gear train produces concomitant rotation of said one or more rotatable pins.

20. The positioning and alignment instrument according to claim 18 wherein said one or more anchoring protrusions are flexible drill bits.

21. The positioning and alignment instrument according to claim 20 wherein said drill bits are removably attachable to said gearbox, thereby permitting selectable use of differently-sized drill bits.

22. The positioning and alignment instrument according to claim 18 wherein said screw is a first screw coupled to a first side of said gear train, and wherein said gearbox further comprises a second screw coupled to a second side of said gear train, such that rotation of either of said first screw and said second screw causes rotational actuation of said gear train for driving said one or more anchoring protrusions into bone.

23. The positioning and alignment instrument according to claim 1 wherein a distal portion of said guidance component is radiolucent.

24. The positioning and alignment instrument according to claim 1 wherein said device guide channel is a first device guide channel, and wherein said positioning and alignment instrument further comprises one or more additional device guide channels, wherein said one or more additional device guide channels are laterally spaced relative to said first device guide channel in a direction that is perpendicular to the rotation axis.

25. The positioning and alignment instrument according to claim 1 wherein said device guide channel is a first device guide channel, and wherein said positioning and alignment instrument further comprises one or more additional device guide channels, wherein said one or more additional device guide channels are laterally spaced relative to said first device guide channel in a direction that is parallel to the rotation axis.

26. The positioning and alignment instrument according to claim 1 wherein said guidance component comprises a two-dimensional array of guide channels, wherein the two-dimensional array of guide channels are arranged in two or more rows and two or more columns, wherein said rows are arranged perpendicular to the rotation axis, and wherein said columns are arranged parallel to the rotation axis.

27. The positioning and alignment instrument according to claim 1 wherein said device guide channel has a diameter suitable for guiding a Kirschner wire.

28. A method of employing fluoroscopy to aligning a device during a medical procedure, the method comprising:
providing a positioning and alignment instrument comprising:
an anchoring component comprising a proximal portion and a distal portion, wherein the proximal portion comprises a handle, and wherein one or more anchoring protrusions extend from a distal end of the distal portion for anchoring the anchoring component into bone, such that a position and an orientation of the anchoring component is fixed relative to the bone when the anchoring component is anchored to the bone; and
a guidance component mechanically supported by the anchoring component, the guidance component comprising a device guide channel for receiving the device and guiding the device towards an insertion location adjacent to the distal end of the distal portion, wherein the guidance component is rotatable relative to the anchoring component about a rotation axis that is located adjacent to the distal end of the anchoring component, such that the insertion location remains adjacent to the distal end of the distal portion under rotation of the guidance component;
after having employed fluoroscopy, in a first direction, to anchor the positioning and alignment instrument;
obtaining fluoroscopy images of the positioning and alignment instrument in a perpendicular direction; and
rotating the guidance component to a desired angle according to the fluoroscopy images;
thereby aligning the device guide channel for subsequent guidance and insertion of the device into the bone.

29. The method according to claim 28 wherein said device guide channel is a first device guide channel, and wherein the guidance component further comprises one or more additional device guide channels, wherein said one or more additional device guide channels are laterally spaced relative to said first device guide channel in a direction that is parallel to said rotation axis, and wherein the method further comprises:
prior to obtaining fluoroscopy images of the positioning and alignment instrument in the perpendicular direction, obtaining fluoroscopy images of the positioning and alignment instrument in the first direction, and selecting a suitable device guide channel for guiding the device to a desired entry location.

30. The method according to claim 28 wherein said device guide channel is a first device guide channel, and wherein the guidance component further comprises one or more additional device guide channels, wherein said one or more additional device guide channels are laterally spaced relative to said first device guide channel in a direction that is perpendicular to said rotation axis, and wherein the method further comprises:
selecting a suitable device guide channel for guiding the device to a desired entry location.

31. The method according to claim 28 wherein the guidance component further comprises a two-dimensional array of guide channels, wherein the two-dimensional array of guide channels are arranged in two or more rows and two or more columns, wherein the rows are arranged perpendicular to the rotation axis, and wherein the columns are arranged parallel to the rotation axis, wherein the method further comprises:
prior to obtaining fluoroscopy images of the positioning and alignment instrument in the perpendicular direction, obtaining fluoroscopy images of the positioning and alignment instrument in the first direction, and selecting a suitable column for guiding the device to a desired entry location; and
when obtaining fluoroscopy images of the positioning and alignment instrument in the perpendicular direction, selecting a suitable row for guiding the device to the desired entry location;
wherein the suitable row and suitable column identify a suitable device guide channel for guiding the device to the desired entry location.

32. The method according to claim 28 wherein the device is a Kirschner wire and the medical procedure involves the insertion and drilling of the Kirschner wire into an intramedullary canal of the bone.

33. The method according to claim 28 wherein the device is a drill bit and the medical procedure involves the insertion and drilling of the drill bit into the bone in order to generate a pilot hole for subsequent insertion of a locking screw into an intramedullary nailing.

34. The method according to claim 28 wherein the perpendicular direction is an anterior-posterior direction.

35. A positioning and alignment instrument for guiding insertion of a device into bone, the positioning and alignment instrument comprising:
an anchoring component comprising a proximal portion and a distal portion, wherein said proximal portion comprises a handle, and wherein one or more anchoring protrusions extend from a distal end of said distal portion for anchoring said anchoring component into the bone, such that a position and an orientation of said anchoring component is fixed relative to the bone when said anchoring component is anchored to the bone; and a guidance component mechanically supported by said anchoring component, said guidance component comprising a device guide channel for receiving the device and guiding the device towards an insertion location adjacent to the distal end of said distal portion;

wherein said guidance component is rotatable relative to said anchoring component about a rotation axis that is located adjacent to the distal end of said anchoring component, such that the insertion location remains adjacent to the distal end of said distal portion under rotation of said guidance component; and wherein said guidance component is pivotally coupled to said anchoring component at a pivot location that is adjacent to said distal end of said distal portion of said anchoring component and adjacent to a distal end of said guidance component.

36. A positioning and alignment instrument for guiding insertion of a device into bone, the positioning and alignment instrument comprising:

an anchoring component comprising a proximal portion and a distal portion, wherein said proximal portion comprises a handle, and wherein one or more anchoring protrusions extend from a distal end of said distal portion for anchoring said anchoring component into the bone, such that a position and an orientation of said anchoring component is fixed relative to the bone when said anchoring component is anchored to the bone; and a guidance component mechanically supported by said anchoring component, said guidance component comprising a device guide channel for receiving the device and guiding the device towards an insertion location adjacent to the distal end of said distal portion;

wherein said guidance component is rotatable relative to said anchoring component about a rotation axis that is located adjacent to the distal end of said anchoring component, such that the insertion location remains adjacent to the distal end of said distal portion under rotation of said guidance component; and wherein a distal portion of said device guide channel is aligned along a device guidance axis, and wherein a proximal portion of said device guide channel deflects outwardly relative to said device guidance axis toward said handle.

37. A positioning and alignment instrument for guiding insertion of a device into bone, the positioning and alignment instrument comprising:

an anchoring component comprising a proximal portion and a distal portion, wherein said proximal portion comprises a handle, and wherein one or more anchoring protrusions extend from a distal end of said distal portion for anchoring said anchoring component into the bone, such that a position and an orientation of said anchoring component is fixed relative to the bone when said anchoring component is anchored to the bone;

a guidance component mechanically supported by said anchoring component, said guidance component comprising a device guide channel for receiving the device and guiding the device towards an insertion location adjacent to the distal end of said distal portion, wherein said guidance component is rotatable relative to said anchoring component about a rotation axis that is located adjacent to the distal end of said anchoring component, such that the insertion location remains adjacent to the distal end of said distal portion under rotation of said guidance component; and a force coupling tool configured to contact said anchoring component and drive said one or more anchoring protrusions into bone upon the application of a force thereto;

wherein said force coupling tool is configured to rotate said one or more anchoring protrusions while said one or more anchoring protrusions are driven into bone.

* * * * *

UNITED STATES PATENT AND TRADEMARK OFFICE
CERTIFICATE OF CORRECTION

PATENT NO. : 10,869,679 B2
APPLICATION NO. : 16/077470
DATED : December 22, 2020
INVENTOR(S) : Ebrahimi et al.

Page 1 of 1

It is certified that error appears in the above-identified patent and that said Letters Patent is hereby corrected as shown below:

In the Claims

Column 13, Line 25 should read:
3. The positioning and alignment instrument according to claim 2 wherein said rotation actuation mechanism is configured to be capable of actuation by a thumb of the first hand while holding said handle with the first hand.

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*